United States Patent [19]

Pepin et al.

[11] Patent Number: 5,531,721
[45] Date of Patent: Jul. 2, 1996

[54] MULTIPLE MEMBER INTRAVASCULAR GUIDE CATHETER

[75] Inventors: Henry J. Pepin, Loretto; Brian J. Scovil, New Hope; Jeffrey M. Welch, Bloomington, all of Minn.

[73] Assignee: SciMed Life Systems, Inc., Maple Grove, Minn.

[21] Appl. No.: 353,142

[22] Filed: Dec. 9, 1994

Related U.S. Application Data

[63] Continuation of Ser. No. 177,701, Jan. 4, 1994, abandoned, which is a continuation of Ser. No. 908,250, Jul. 2, 1992, abandoned.

[51] Int. Cl.$^6$ .................................................. A61M 25/00
[52] U.S. Cl. ........................ 604/282; 604/280; 138/120
[58] Field of Search ................................. 604/264, 280, 604/282; 128/656–658, 772; 138/120, 155

[56] References Cited

U.S. PATENT DOCUMENTS

| | | | |
|---|---|---|---|
| 3,184,353 | 5/1965 | Balamuth et al. | 156/73 |
| 3,485,234 | 12/1969 | Stevens | 128/2 |
| 3,860,468 | 1/1975 | Scherer | 156/304.2 |
| 3,985,601 | 10/1976 | Panagrossi | 156/229 |
| 4,003,382 | 1/1977 | Dyke | 128/349 |
| 4,239,575 | 12/1980 | Leatherman | 156/272 |
| 4,251,305 | 2/1981 | Becker et al. | 156/86 |
| 4,323,071 | 4/1982 | Simpson et al. | 128/343 |
| 4,335,723 | 6/1982 | Patel | 128/349 |
| 4,385,635 | 5/1983 | Ruiz | 128/658 |
| 4,407,691 | 10/1983 | Ishu et al. | 156/304.2 |
| 4,419,095 | 12/1983 | Nebergall et al. | 604/96 |
| 4,425,919 | 1/1984 | Alston, Jr. et al. | 128/658 |
| 4,531,943 | 7/1985 | Van Tassel et al. | 604/280 |
| 4,547,193 | 10/1985 | Rydell | 604/282 |
| 4,551,292 | 11/1985 | Fletcher et al. | 264/139 |
| 4,563,181 | 1/1986 | Wijayarathna et al. | 604/280 |
| 4,586,923 | 5/1986 | Gould et al. | 604/95 |
| 4,636,346 | 1/1987 | Gold et al. | 264/139 |
| 4,661,095 | 4/1987 | Taller et al. | 604/103 |
| 4,690,175 | 9/1987 | Ouchi et al. | 138/131 |
| 4,739,768 | 4/1988 | Engelson | 128/658 |
| 4,759,748 | 7/1988 | Reed | 604/95 |
| 4,790,831 | 12/1988 | Skribiski | 604/282 |
| 4,801,297 | 1/1989 | Mueller | 604/280 |
| 4,813,930 | 3/1989 | Elliott | 604/53 |
| 4,817,613 | 4/1989 | Jaraczewski et al. | 128/658 |
| 4,822,345 | 4/1989 | Danforth | 604/282 |
| 4,838,879 | 6/1989 | Tanabe et al. | 604/280 |
| 4,842,590 | 6/1989 | Tanabe et al. | 604/282 |
| 4,846,814 | 7/1989 | Ruiz | 604/281 |
| 4,863,442 | 9/1989 | DeMello et al. | 604/282 |
| 4,884,579 | 12/1989 | Engelson | 128/772 |

(List continued on next page.)

FOREIGN PATENT DOCUMENTS

| | | |
|---|---|---|
| 0334640 | 9/1989 | European Pat. Off. . |
| 0405658A2 | 1/1991 | European Pat. Off. . |
| 0420993A1 | 4/1991 | European Pat. Off. . |
| 2140755 | 2/1973 | Germany . |
| 58-29616 | 2/1983 | Japan . |
| 58-29617 | 2/1983 | Japan . |
| 0749753 | 5/1956 | United Kingdom . |
| WO90/11793 | 4/1990 | WIPO . |
| WO92/15356 | 2/1992 | WIPO . |

*Primary Examiner*—Corrine M. McDermott
*Attorney, Agent, or Firm*—Kinney & Lange

[57] ABSTRACT

An intravascular guide catheter includes a main shaft member, a bond member, an intermediate shaft member and a terminal shaft member. The main shaft has a proximal end and a mating distal end. The bond ring includes a mating proximal end, which is joined to the mating distal end of the main shaft member, and a mating distal end. The intermediate shaft member includes a mating proximal end, which is joined to the mating distal end of the bond member, and a mating distal end. The terminal shaft member includes a mating proximal end, which is joined to the mating distal end of the intermediate member, and a distal end. The main and intermediate shaft members have wire braiding reinforcing layers. The material of the intermediate shaft member has a greater hardness than the material of the terminal shaft member and a lower hardness than the material of the main shaft member.

39 Claims, 3 Drawing Sheets

U.S. PATENT DOCUMENTS

| | | | |
|---|---|---|---|
| 4,886,506 | 12/1989 | Lovgren et al. | 604/280 |
| 4,898,591 | 2/1990 | Jang et al. | 604/282 |
| 4,913,701 | 3/1990 | Tower | 604/103 |
| 4,921,482 | 5/1990 | Hammerslag et al. | 604/95 |
| 4,923,659 | 5/1990 | Kunz | 156/304.2 |
| 4,961,731 | 10/1990 | Bodicky et al. | 604/264 |
| 4,983,169 | 1/1991 | Furukawa | 604/164 |
| 4,987,018 | 1/1991 | Dickinson et al. | 428/36.9 |
| 5,004,456 | 4/1991 | Botterbusch et al. | 604/53 |
| 5,017,259 | 5/1991 | Kohsai | 156/294 |
| 5,037,404 | 8/1991 | Gold et al. | 604/282 |
| 5,045,072 | 9/1991 | Castillo et al. | 604/280 |
| 5,078,702 | 1/1992 | Pomeranz | 604/280 |
| 5,160,559 | 11/1992 | Scovil et al. | 156/73.6 |
| 5,163,431 | 11/1992 | Griep | 128/658 |
| 5,254,107 | 10/1993 | Soltesz | 604/282 |
| 5,279,596 | 1/1994 | Castaneda et al. | 604/282 |

MULTIPLE MEMBER INTRAVASCULAR GUIDE CATHETER

This is a Continuation of application Ser. No. 08/177,701, filed Jan. 4, 1994, now abandoned, which is a Continuation of application Ser. No. 07/908,250, filed Jul. 2, 1992, which is abandoned.

BACKGROUND OF THE INVENTION

The present invention relates to the field of angioplasty. In particular, the present invention is a guide catheter having three principal segments, with each segment having a different degree of flexibility.

Angioplasty has gained wide acceptance in recent years as an efficient and effective method for treating various types of vascular diseases. In particular, angioplasty is widely used for opening stenoses in the coronary arteries, although it is also used for treatment of stenoses in other parts of the vascular system.

The most widely used form of angioplasty makes use of a guide catheter positioned within the vascular system of a patient. The distal end of the guide catheter is inserted into the femoral artery located in the groin of the patient and pushed distally up through the vascular system until the distal end of the guide catheter is located in the ostium of the coronary artery. The distal end of the guide catheter is normally curved so that the distal tip of the guide catheter is more easily directed to the coronary ostium of the patient. The distal tip of the guide catheter is typically formed from relatively soft, flexible material to avoid trauma to arterial vessels, and allow flexing of the distal tip to aid the guide catheter in traversing desired arterial branches. That portion of the guide catheter proximal to the distal tip is typically stiffer to enhance torqueability and pushability which further assist the guide catheter in traversing the patient's vascular system. The proximal end of the guide catheter protrudes outside the patient's body to provide an entryway for subsequent insertion of additional angioplasty devices. The additional angioplasty devices include dilatation catheters such as non-over-the-wire and over-the-wire balloon catheters.

Angiographic catheters having soft, flexible distal tips and stiffer proximal segments are generally known. U.S. Pat. No. 4,385,635 to Ruiz discloses one such catheter. The catheter includes a soft tip or terminal zone, an intermediate zone and a main fully reinforced length. An exterior jacket which is relatively soft and flexible extends along the entire length of the catheter. Within the main length of the jacket is a reinforcing tube which is adhered to the inside diameter of the exterior jacket. The reinforcing tube is relatively rigid to provide torque control. In the intermediate zone, the exterior jacket is tapered so that it is enlarged in cross-section at the distal portion of the intermediate zone. The reinforcing within the intermediate zone is tapered to provide an easy transition between the main fully reinforced length and the soft tip. The reinforcing tube tapers to zero such that the soft tip consists entirely of the exterior jacket. The intermediate zone provides decreasing stiffness between the main length and the soft tip of the angiographic catheter.

U.S. Pat. No. 5,045,072 to Castillo et al. discloses a catheter having a catheter body, a distal tip and a transition zone that connects the distal tip to the catheter body. The transition zone is free of tubular reinforcing braid, while the catheter body carries such reinforcing braid in its interior. The distal tip is heat bonded to a distal end of the transition zone which is in turn heat bonded at its other end to the catheter body. The distal tip is made of a first polyurethane formulation while the catheter body and transition zone are made of a second different polyurethane formulation. Both the catheter body and the transition zone are flexible, however, the distal tip exhibits greater flexibility and lower durometer than the rest of the catheter.

SUMMARY OF THE INVENTION

The present invention is an intravascular catheter that includes a main shaft member, an intermediate shaft member and a terminal shaft member. The main shaft member has a proximal end and a mating distal end and is formed of a material having a first hardness. The intermediate shaft member includes a mating proximal end, which is joined to the mating distal end of the main member, and a mating distal end. The intermediate member is formed of a material having a second hardness which is lower than the first hardness of the main member. The terminal shaft member includes a mating proximal end, which is joined to the mating distal end of the intermediate member, and a distal end. The terminal member is formed of a material having a third hardness which is lower than the second hardness of the intermediate member.

Both the main and intermediate members are formed of elastomeric tubular elements having wire braiding reinforcing layers embedded therein. The main and intermediate members are joined to one another through a bond member formed of an elastomeric tubular element that is free of a wire braiding reinforcing layer. The terminal member is also formed of an elastomeric tubular element that is free of a wire braiding reinforcing layer.

The tubular elements of the main, bond, intermediate and terminal members define an intravascular guide catheter having a through lumen that extends from the proximal end of the main member to the distal end of the terminal member. The through lumen defines a passageway for the insertion of dilatation catheters into the vascular system of a patient. The distal end of the intravascular guide catheter is curved to so that the guide catheter is more easily directed to the coronary ostium of the patient.

This intravascular guide catheter having three principal segments, with each segment having a different degree of flexibility is a relatively efficient design. The main shaft member has sufficient hardness to provide rigidity to enhance the torqueability and pushability of the guide catheter. The intermediate shaft member has a lower hardness than the main member and therefore is more flexible, to allow the curved distal portion of the guide catheter to easily conform to the arteriovenous system of the patient as the guide catheter traverses the femoral artery. In addition, the wire braiding reinforcing layer of the intermediate member provides enough rigidity to the intermediate member to enhance the torqueability and pushability of that portion of the guide catheter. The terminal shaft member has a lower hardness than the intermediate member so as to be sufficiently flexible to avoid trauma to arterial vessels. In addition, during assembly of the guide catheter, the bond member acts as a melt adhesive to promote adhesion between the main shaft member and the intermediate shaft member. When heated, the bond member forms a molten pool of elastomeric material. This molten pool of material allows the molecular chains at the bond site (i.e., the area where the main and intermediate shaft members are joined) to readily bond to each other to create a homogeneous bond.

Other advantages and features of the present invention will be apparent from the following description of the preferred embodiment taken in conjunction with the accompanying drawings.

While the above-identified figures set forth a preferred embodiment, other embodiments of the present invention are also contemplated as noted in the discussion. In all cases, this disclosure presents illustrated embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity. In addition, the use of such relational terms as left/right, upper/lower, or horizontal/vertical, etc. are used herein for reference purposes only and are not intended to be limiting features of the invention disclosed.

DETAILED DESCRIPTION OF THE PREFERRED EMBODIMENTS

Figure 1:
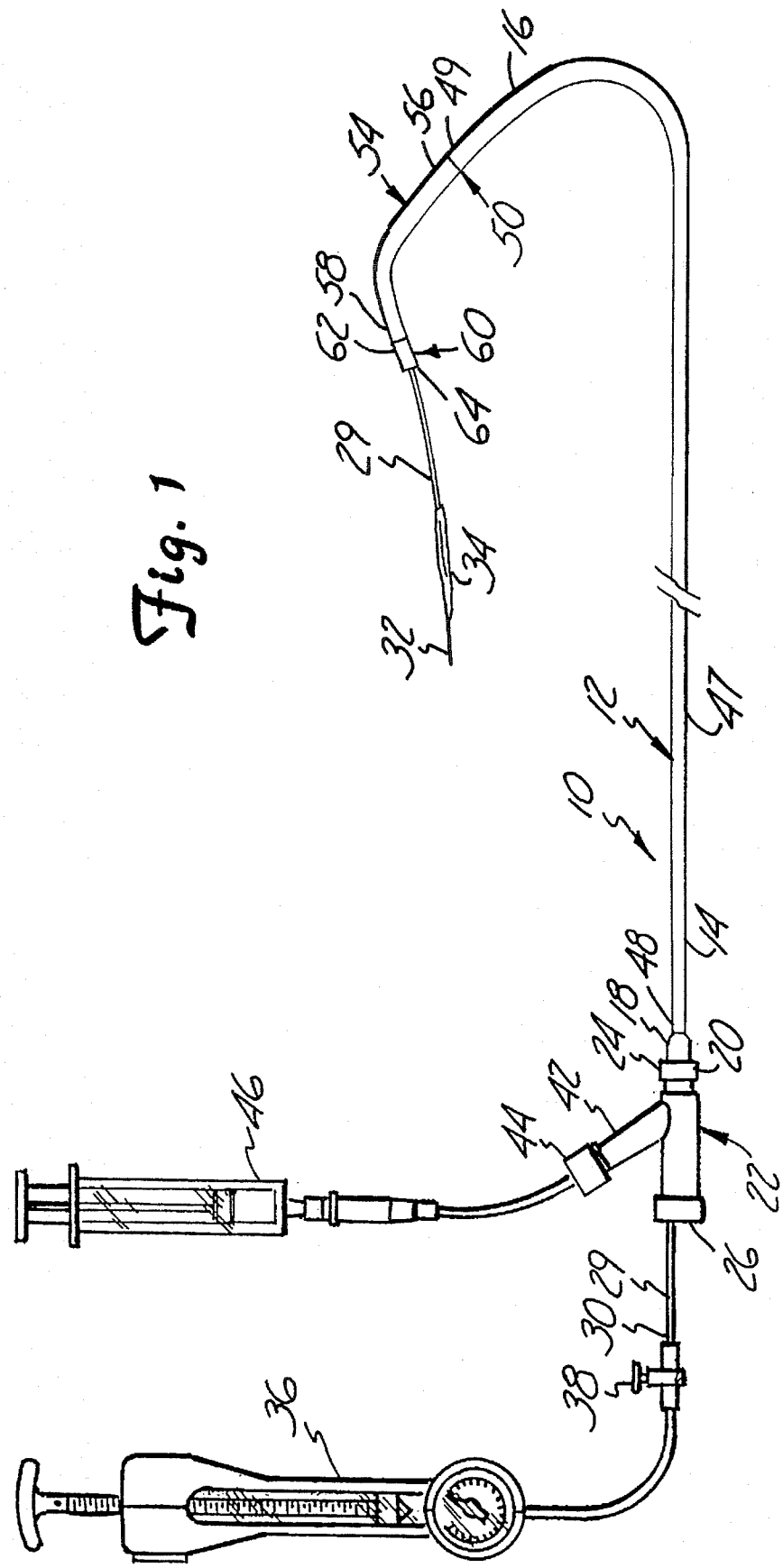
FIG. 1 is a side elevational view of an angioplasty catheter system including an intravascular guide catheter of the present invention.

An angioplasty catheter system 10 including an intravascular guide catheter 12 of the present invention is illustrated generally in FIG. 1. The guide catheter 12 includes a proximal portion 14 and a curved distal portion 16. A through lumen 15 (see FIG. 2) extends along the entire length of the guide catheter 12.

A manifold coupler 18 is secured to the proximal portion 14 of the guide catheter 12. A threaded luer lock fitting 24 releasably secures the manifold coupler 18 to a distal end 20 of a Y-adaptor manifold 22. A proximal end 26 of the Y-adaptor manifold 22 includes a Touhy-Borst compression seal 28 which forms a fluid-tight seal around a shaft of an angioplasty dilatation balloon catheter 29 (shown extending through the guide catheter 12).

The dilatation catheter 29 has a proximal end 30 and a distal end 32 with a balloon 34 formed thereon. The balloon 34 is inflatable by an inflation device 36 connected to the proximal end 30 of catheter 29 by way of a three-way valve fitting 38. The Y-adaptor 22 further includes a side port 42 having a Touhy-Borst compression seal 44. The side port 42 is adapted to receive a syringe 46 containing a radiopaque dye which is injected through the lumen 15 of guide catheter 12 (via Y-adaptor 22) to the coronary arteries in a conventional manner.

Figure 2:
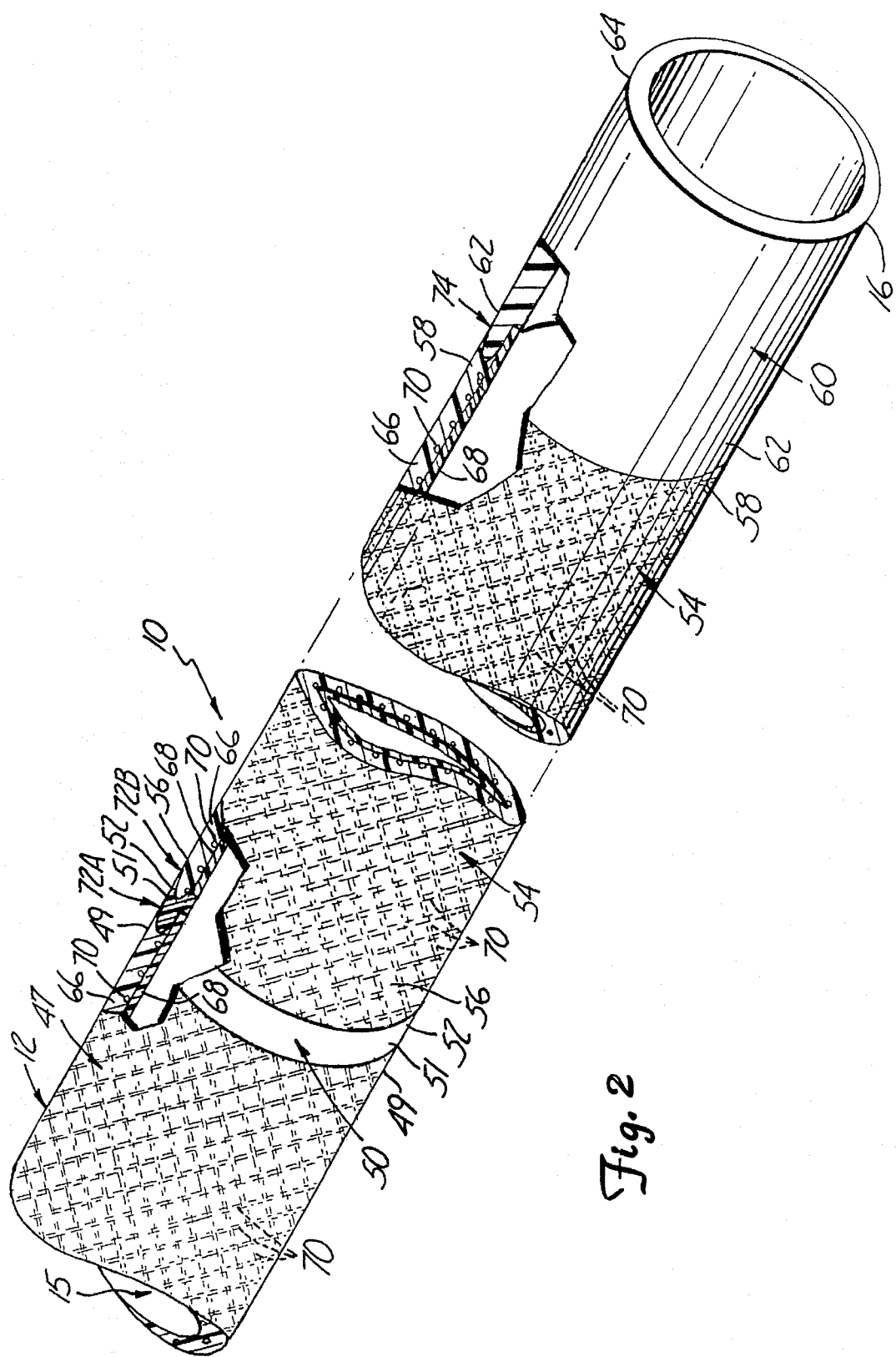
FIG. 2 is a greatly enlarged perspective view of a distal portion of the guide catheter, with some parts broken away and shown in section to illustrate each of the parts of the guide catheter.
Figure 3:
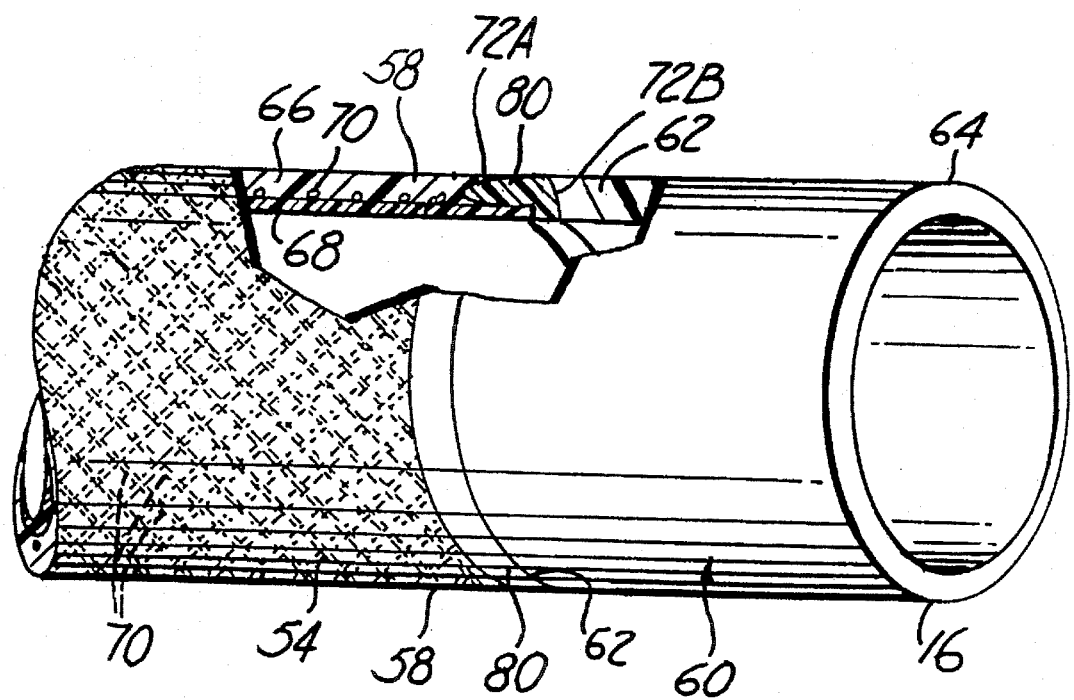
FIG. 3 is a greatly enlarged perspective view of an alternate embodiment of a distal portion of the guide catheter, with some parts broken away and shown in section to illustrate each part of the guide catheter.

As seen best in FIG. 2, the guide catheter 12 includes a main shaft member 47 having a proximal end 48 (see FIG. 1) and a mating distal end 49. A bond member, such as a bond ring 50, includes a mating proximal end 51, which is joined to the mating distal end 49 of the main shaft member 47, and a mating distal end 52. An intermediate shaft member 54 of the guide catheter 12 includes a mating proximal end 56, which is joined to the mating distal end 52 of the bond ring 50, and a mating distal end 58. A terminal shaft member 60 has a mating proximal end 62, which is joined to the mating distal end 58 of the intermediate member 54, and a distal end 64.

Preferably, the main shaft member 47 and the intermediate shaft member 54 are each formed of an elastomeric tubular element having an outer layer 66, an inner layer 68, and a reinforcing layer 70 embedded therebetween. In one embodiment, the outer layer 66 is preferably formed of a polyether block amide, such as PEBAX® available from ATOCHEM, Inc. (Glen Rock, N.J.) and a radiopaque compound, such as bismuth subcarbonate, and the inner layer 68 is a coating of lubricous material, such as TEFLON® available from E.I. DuPont Nemours & Co. (Wilmington, Del.). The reinforcing layers 70 are a wire braiding that extends from the proximal end 48 to the mating distal end 49 of main member 47 and from the mating proximal end 56 to the mating distal end 58 of intermediate member 54. In one embodiment the wire braiding of the reinforcing layers 70 is formed of 2/1000th of an inch diameter stainless steel wire. The terminal shaft member 60 is also an elastomeric tubular element preferably formed of a polyether block amide, such as PEBAX® and a radiopaque compound, such as bismuth subcarbonate. However, the terminal member 60 is free of the wire braid reinforcing layer and lubricous coating. In addition, the bond ring 50 is an elastomeric tubular element preferably formed of a polyether block amide, such as PEBAX® and a radiopaque compound, such as bismuth subcarbonate. The bond ring 50 is free of the wire braid reinforcing layer and lubricous coating.

The material of the tubular element of the main shaft member 47 contains a first weight percent (i.e., approximately 30%) of the radiopaque compound. The material of the tubular element of the intermediate shaft member 54 contains a second weight percent (i.e., approximately 35%) of the radiopaque material which is greater than the first weight percent of the main shaft member 47. In addition, the material of the tubular element of the terminal shaft member 60 contains a third weight percent (i.e., approximately 36%) of the radiopaque material which is greater than the second weight percent of the intermediate shaft member 54.

The material from which the main shaft member 47 is formed has a first hardness value. The material from which the intermediate shaft member 54 is formed has a second hardness value which is lower than the first hardness value of the main member 47. In addition, the material from which the terminal shaft member 60 is formed has a third hardness value which is lower than the second hardness value of the intermediate member 54. In one embodiment, the first, second and third hardness values of the material before it is formed into the main, intermediate and terminal shaft members 47, 54 and 60, respectively, are durometers of 63, 40 and 35, respectively. The material from which the bond ring 50 is formed is a blend of the sixty-three durometer material of the main shaft member 47 and the forty durometer material of the intermediate shaft member 54. Hence, the material used to form the bond ring 50 has a durometer (hardness value) of approximately 51.5 before it is formed into the bond ring 50, and as such, has a hardness value greater than the second hardness value of the intermediate member 54 and a hardness value less than the first hardness value of the main member 47. Because the bond ring 50 is a blend of the materials of the main and intermediate shaft members 47 and 54, the material of the tubular element of the bond ring 50 contains approximately a 32.5 weight percent of the radiopaque compound.

The mating distal end 49 of main member 47 and the mating proximal end 51 of the bond ring 50 are joined together into a lap joint bond 72A. The mating distal end 52 of the bond ring 50 and the mating proximal end 56 of the intermediate member 54 are joined together into a lap joint bond 72B. The lap joint bonds 72A and 72B securely fasten the intermediate member 54, the bond ring 50 and the main member 47 together. Likewise, the mating distal end 58 of the intermediate member 54 and the mating proximal end 62 of terminal member 60 are joined together into a lap joint bond 74 which securely fastens the intermediate member 58 and the terminal member 60 together. The lap joint bonds 72A, 72B and 74 as well as the terminal member 60, intermediate member 54, main member 47 and bond ring 50 are all formed according to the method and manner described in U.S. patent application METHOD FOR FORMING A GUIDE CATHETER TIP BOND, Ser. No. 07/761,716, filed on Sep. 17, 1991, which is a Continuation-in-Part of U.S. patent application METHOD FOR FORMING A GUIDE CATHETER TIP BOND, Ser. No. 07/606,090, filed on Oct. 31, 1990, which are both incorporated by reference herein. Preferably, the lap joint bonds 72A and 72B are formed at the same time. The lap joint bond 74 is preferably formed subsequent to the lap joint bonds 72A and 72B. The lap joint bonds 72A and 72B are preferably formed by heating the bond site (i.e., the area where the main shaft member 47, the bond ring 50 and the intermediate shaft member 54 meet) for approximately 25 seconds at a temperature of 535°+60° F./-10° F. Preferably, pressure is applied at the end of the 25 second cycle to eject the now joined members. The lap joint bond 74 is preferably formed by heating the bond site (i.e., the area where the intermediate shaft member 54 and terminal shaft member 60 meet) for approximately 10 seconds at a temperature of 415°±5° F. At the expiration of the 10 second time interval, pressure (i.e., a uniform, longitudinal force) of 15±1 p.s.i. is applied against the terminal member 60 (pressing the terminal member 60 into the intermediate member 54) for approximately 5 seconds while the bond site is continuously heated at the above-referenced temperature.

With the guide catheter 12 in its completed state, the terminal member 60 has a length of 0.125"±0.025" the intermediate member 54 has a length of 0.787"±0.039" the bond ring 50 has a length of 0.020"+0.010" and the main member 47 has a usable length of 38.5"+0.787"/-1.181".

The intravascular guide catheter 12 of the present invention is a relatively efficient design. The main shaft member 47 has sufficient hardness to provide rigidity to enhance the torqueability and pushability of the guide catheter 12. The intermediate shaft member 54 has a lower hardness than the main member 47 and therefore is more flexible, to allow the curved distal portion 16 of the guide catheter 12 to easily conform to the arteriovenous system of a patient as the guide catheter 12 traverses the femoral artery. In addition, the wire braiding reinforcing layer 70 of the intermediate member 54 provides enough rigidity to the intermediate member 54 to enhance the torqueability and pushability of that portion of the guide catheter 12. The terminal shaft member 60 has a lower hardness than the intermediate member 54 so as to be sufficiently flexible to avoid trauma to arterial vessels.

In addition, during assembly of the guide catheter 12, the bond ring 50 acts as a melt adhesive to promote adhesion between the main shaft member 47 and the intermediate shaft member 54. When heated, the bond ring 50 forms a molten pool of elastomeric material. This molten pool of material allows the molecular chains at the bond site (i.e., the area where the main shaft member 47 and the intermediate shaft member 54 are joined) to readily bond to each other to create a homogeneous bond. Moreover, the differing radiopaqueness of the main, intermediate and terminal members 47, 54 and 60, respectively, permits visibility of the guide catheter 12 in a fluoroscope so that the guide catheter 12 may be precisely positioned within the vascular system of a patient.

Although the present invention has been described with reference to preferred embodiments, workers skilled in the art will recognize that changes may be made in form and detail without departing from the spirit and scope of the invention. For example, a bond ring 80, similar to the bond ring 50 between the main member 47 and the intermediate member 54, could be used between the intermediate member 54 and the terminal member 60. The material used to from this bond ring would be a blend of the materials from which the intermediate member 54 and the terminal member 60 are formed.

What is claimed is:

1. An intravascular catheter comprising:

an elongate shaft formed from at least three discrete tubular shaft members which have been joined together, the shaft including:

a main shaft member formed of a material having a first hardness, the main shaft member including a proximal end and a mating distal end;

an intermediate shaft member formed of an elastomeric material having a first reinforcing layer embedded therein and having a second hardness which is lower than the first hardness of the material of the main shaft member, the intermediate member including a mating proximal end, which is secured to the mating distal end of the main member, and a mating distal end, the first reinforcing layer being made of a wire braiding that extends from the mating proximal end to the mating distal end of the intermediate member; and a terminal shaft member formed of a material free of a reinforcing layer and having a third hardness which is lower than the second hardness of the material of the intermediate shaft member, the terminal member including a mating proximal end, which is secured to the mating distal end of the intermediate member, and a distal end.

2. The catheter of claim 1 wherein the main shaft member is formed of an elastomeric tubular element having a second reinforcing layer embedded therein.

3. The catheter of claim 2 wherein the second reinforcing layer is a wire braiding that extends from the proximal end to the mating distal end of the main shaft member.

4. The catheter of claim 3 wherein the wire braiding is formed of a metal material.

5. The catheter of claim 2 wherein the intermediate shaft member is formed of an elastomeric tubular element having the first reinforcing layer embedded therein, and the second reinforcing layer embedded in the main shaft member terminates adjacent the distal end of the main shaft member such that the second reinforcing layer in the main shaft member is separate from the first reinforcing layer of the intermediate member.

6. The catheter of claim 1, and further including a through lumen which extends from the proximal end of the main member to the distal end of the terminal member, the through lumen defining a passageway for insertion of an intravascular device.

7. The catheter of claim 1 wherein the intravascular catheter is an angioplasty guide catheter.

8. The catheter of claim 1 wherein the first hardness is a Shore D durometer of 63, wherein the second hardness is a Shore D durometer of 40 and wherein the third hardness is a Shore D durometer of 35.

9. The catheter of claim 1 and further including a first bond member disposed between the mating distal end of the main member and the mating proximal end of the intermediate member.

10. The catheter of claim 9 wherein the first bond member is formed of a material that is a blend of the materials of the main member and intermediate members.

11. The catheter of claim 9 wherein the first bond member has a fourth hardness that is less than the first hardness of the material of the main member and greater than the second hardness of the material of the intermediate member.

12. The catheter of claim 9 and further including:
a second bond member disposed between the mating distal end of the intermediate member and the mating proximal end of the terminal member.

13. The catheter of claim 12 wherein the second bond member has a fifth hardness that is less than the second hardness of the material of the intermediate member and greater than the third hardness of the material of the terminal member.

14. The catheter of claim 1 wherein the intermediate shaft member has a uniform flexibility throughout its length.

15. An intravascular catheter comprising:
an elongate shaft formed from at least four discrete tubular shaft members which have been joined together, the shaft including:
a main shalt member having a first flexibility along its length and being formed of a material having a first hardness, the main shaft member including a proximal end and a mating distal end;
an intermediate shaft member having a second flexibility along its length and being formed of a material having a second hardness which is lower than the first hardness of the material of the main shaft member, the intermediate member including a mating proximal end and a mating distal end;
a terminal shaft member formed of a material having a third hardness which is lower than the second hardness of the material of the intermediate shaft member, the terminal member including a mating proximal end, which is secured to the mating distal end of the intermediate shaft member, and a distal end; and
a first bond member melding the mating distal end of the main shaft member and the mating proximal end of the intermediate shaft member, wherein the bond member has a fourth hardness intermediate the first hardness of the main shaft member and the second hardness of the intermediate shaft member.

16. The catheter of claim 15 wherein the first bond member has a fourth hardness that is less than the first hardness of the material of the main member and greater than the second hardness of the material of the intermediate member.

17. The catheter of claim 15 and further including:
a second bond member formed of a material free of a reinforcing layer and secured between the mating distal end of the intermediate shaft member and the mating proximal end of the terminal shaft member.

18. The catheter of claim 17 wherein the second bond member has a fifth hardness that is less than the second hardness of the material of the intermediate member and greater than the third hardness of the material of the terminal member.

19. The catheter of claim 15 wherein the main shaft member has a first reinforcing layer embedded therein and the intermediate shaft member has a second reinforcing layer embedded therein, wherein the first reinforcing layer of the main shaft member terminates adjacent the distal end of the main shaft member such that the first reinforcing layer of the main shaft member is separate from the second reinforcing layer of the intermediate member.

20. The catheter of claim 15 wherein the first bond member is formed from a single material into the shape of an annular ring.

21. The intravascular catheter of claim 15 wherein the first bond member is a single layer of material formed from a blend of substantially equal portions of the material forming the main shaft member and of the material forming the intermediate shaft member so that the first bond member has a hardness approximately medial the first hardness and the second hardness.

22. An intravascular catheter comprising:
an elongate shall formed from at least three discrete tubular shaft members which have been joined together, the shaft including:
a main shaft member having a side wall formed of a material having a first reinforcing layer embedded therein and having a first hardness, the main shaft member including a proximal end and a mating distal end wherein the first reinforcing layer includes a wire braiding that extends from the proximal end to the mating distal end of the main shaft member;
an intermediate shaft member having a side wall formed of a material having a second reinforcing layer embedded therein, and having a second hardness which is lower than the first hardness of the material of the main shaft member, the intermediate member including a mating proximal end, which is secured to the mating distal end of the main member, and a mating distal end, wherein the second reinforcing layer includes a wire braiding that extends from the mating proximal end to the mating distal end of the intermediate shaft member; and
a terminal shaft member formed of a material free of a reinforcing layer and having a third hardness which is lower than the second hardness of the material of the intermediate shaft member, the terminal member including a mating proximal end, which is secured to the mating distal end of the intermediate member, and a distal end,
wherein the first reinforcing layer of the main shaft member terminates adjacent the distal end of the main shaft member such that the first reinforcing layer of the main shaft member is separate from the second reinforcing layer of the intermediate shaft member and,
wherein a through lumen extends from the proximal end of the main member to the distal end of the terminal member, the through lumen defining a passageway for insertion of an intravascular device.

23. An intravascular catheter comprising:
an elongate shaft formed from at least four discrete tubular shaft members which have been joined together, the shaft including:
a main shaft member formed of a material having a first reinforcing layer embedded therein and having a first hardness, the main shaft member including a proximal end and a mating distal end;

an intermediate shaft member formed of a material having a second reinforcing layer embedded therein and having a second hardness which is lower than the first hardness of the material of the main shall member, the intermediate member including a mating proximal end, which is secured to the mating distal end of the main member, and a mating distal end;

a bond member being formed of a material having a third hardness which is lower than the second hardness of the material of the intermediate member, the bond member including a mating proximal end, which is secured to the mating end of the intermediate shaft member, and a mating distal end; and a terminal shaft member formed of a material free of a reinforcing layer and having a fourth hardness which is lower than the third hardness of the material of the bond member, the terminal member including a mating proximal end, which is secured to the mating distal end of the bond member, and a distal end.

24. An intravascular catheter comprising:

an elongate shaft formed from at least four discrete tubular shaft members which have been joined together, the shaft including:

a main shaft member formed of a material having a first hardness, the main shaft member including a proximal end and a mating distal end;

a bond member having the shape of an annular ring and including a mating proximal end, which is secured to the mating distal end of the main member, and a mating distal end;

an intermediate shaft member formed of a material having a first reinforcing layer embedded therein and having a second hardness which is lower than the first hardness of the material of the main shaft member, the intermediate member including a mating proximal end, which is secured to the mating distal end of the bond member, and a mating distal end; and a terminal shaft member formed of a material free of a reinforcing layer and having a third hardness which is lower than the second hardness of the material of the intermediate shaft member, the terminal member including a mating proximal end, which is secured to the mating distal end of the intermediate member, and a distal end.

25. An intravascular catheter comprising:

an elongate shaft made of at least five discrete tubular members including:

a main shaft member formed of a material having a first reinforcing layer embedded therein and having a first hardness, the main shaft member including a proximal end and a mating distal end;

a first bond member formed of a material free of a reinforcing layer and having a second hardness which is less than the first hardness of the main member, the first bond member including a mating proximal end, which is secured to the mating distal end of the main member, and a mating distal end;

an intermediate shaft member formed of a material having a third hardness which is lower than the second hardness of the material of the first bond member, the intermediate member including a mating proximal end, which is secured to the mating distal end of the first bond member, and a mating distal end;

a second bond member formed of a material free of a reinforcing layer and having a fourth hardness which is lower than the third hardness of the material of the intermediate member, the second bond member including a mating proximal end, which is secured to the mating distal end of the intermediate shaft member, and a mating distal end; and a terminal shaft member formed of a material free of a reinforcing layer and having a fifth hardness which is lower than the fourth hardness of the material of the second bond member, the terminal member including a mating proximal end, which is secured to the mating distal end of the second bond member, and a distal end.

26. An intravascular catheter comprising:

an elongate shaft formed from at least four discrete tubular shaft members which have been joined together, the shaft including:

a main shaft member formed of a material having a first reinforcing layer embedded therein and having a first hardness, the main shaft member including a proximal end and a mating distal end, the first reinforcing layer terminating adjacent the mating distal end;

a first bond member including a mating proximal end, which is secured to the mating distal end of the main shaft member, and a mating distal end;

an intermediate shaft member formed of a material having a second reinforcing layer embedded therein and being separate from the first reinforcing layer of the main shaft member and the intermediate shaft member being formed of a material having a second hardness which is lower than the first hardness of the material of the main shaft member, the intermediate member including a mating proximal end, which is secured to the mating distal end of the first bond member, and a mating distal end; and a terminal shaft member formed of a material having a third hardness which is lower than the second hardness of the material of the intermediate shaft member, the terminal member including a mating proximal end, which is secured to the mating distal end of the intermediate shaft member, and a distal end.

27. An intravascular catheter comprising:

an elongate shaft formed from at least four discrete tubular shaft members which have been joined together, the shaft including:

a main shaft member formed of a material having a first hardness, the main shaft member having a first flexibility along its length and including a proximal end and a mating distal end;

an intermediate shaft member formed of a material having a second hardness which is lower than the first hardness of the material of the main shaft member, the intermediate member having a second flexibility along its length including a mating proximal end, which is secured to the mating distal end of the main member, and a mating distal end;

a terminal shaft member formed of a material having a third hardness which is lower than the second hardness of the intermediate shaft member, the terminal shaft member having a third flexibility along its length and including a mating proximal end; and a bond member melding the mating distal end of the intermediate shaft member and the mating proximal end of the terminal shaft member, the bond member being formed of a single layer of material free of a reinforcing layer and the bond member defining a through lumen and having a fourth hardness intermediate the second hardness of the intermediate shaft member and the third hardness of the terminal shaft member.

28. The catheter of claim 27 wherein the intermediate shaft member has a reinforcing layer embedded therein, the reinforcing layer terminating at the mating proximal end and the mating distal end of the intermediate shaft member.

29. The catheter of claim 28 wherein each of the main and intermediate shaft members include an inner layer having a smooth and continuous inner surface defining a through lumen.

30. The catheter of claim 27 wherein the material forming the bond member is a blend of substantially equal portions of the material forming the intermediate shaft member and the material forming the terminal shaft member so that the fourth hardness of the bond member is medial the second hardness and the first hardness.

31. An intravascular catheter comprising:
an elongate shaft formed from at least three discrete tubular members which have been joined together, the shaft including:
a first tubular member formed of a material having a first reinforcing layer embedded therein and having a first hardness, the first tubular member including a proximal end and a mating distal end, the first reinforcing layer terminating adjacent the mating distal end;
a second tubular member including a mating proximal end, which is secured to the mating distal end of the first tubular member, and a mating distal end;
a third tubular member formed of a material having a second reinforcing layer embedded therein and having a second hardness which is lower than the first hardness of the material of the first tubular member, the third tubular member including a mating proximal end, which is secured to the mating distal end of the; second tubular member, and a distal end, the second reinforcing layer terminating adjacent the mating proximal end.

32. The catheter of claim 31 wherein the second tubular member is formed of a material free of a reinforcing layer.

33. The catheter of claim 31 and further comprising:
a fourth tubular member formed of a material free of a reinforcing layer and having a mating proximal end secured to the distal end of the third tubular member.

34. An intravascular catheter comprising:
an elongate shaft made of at least five discrete tubular members including:
a first main tubular member formed of a material having a first hardness, the main tubular member including a proximal end and a mating distal end;
a second tubular member formed of a material free of a reinforcing layer and having a second hardness which is less than the first hardness of the main member, the second tubular member including a mating proximal end, which is secured to the mating distal end of the main member and a mating distal end;
a third tubular member formed of an elastomeric material having a first reinforcing layer embedded therein and having a third hardness which is less than the second hardness of the second tubular member, the third tubular member including a mating proximal end, which is secured to the mating distal end of the second tubular member, and a mating distal end;
a fourth tubular member formed of a material free of a reinforcing layer and having a fourth hardness which is less than the third hardness of the material of the third tubular member, the fourth tubular member including a mating proximal end, which is secured to the mating distal end of the third tubular member, and a mating distal end; and
a fifth terminal tubular member formed of a material free of a reinforcing layer and having a fifth hardness which is less than the fourth hardness of the material of the fourth tubular member, the terminal member including a mating proximal end, which is secured to the mating distal end of the fourth tubular member, and a distal end.

35. An intravascular catheter comprising:
an elongate shaft made of at least four discrete tubular members including:
a first main tubular member formed of a material having a first hardness, the main tubular member including a proximal end and a mating distal end;
a second tubular member formed of an elastomeric material having a first reinforcing layer embedded therein and having a second hardness which is lower than the first hardness of the material of the main tubular member, the second tubular member including a mating proximal end, which is secured to the mating distal end of the main member, and a mating distal end;
a third tubular member formed of a material free of a reinforcing layer and having a third hardness which is lower than the second hardness of the material of the second tubular member, the third tubular member including a mating proximal end, which is secured to the mating distal end of the second tubular member, and a mating distal end; and
a fourth terminal tubular member formed of a material free of a reinforcing layer and having a fourth hardness which is lower than the third hardness of the material of the third tubular member, the terminal member including a mating proximal end, which is secured to the mating distal end of the third tubular member, and a distal end.

36. An intravascular catheter comprising:
an elongate shaft made of at least five discrete tubular members including:
a first main tubular member formed of a material having a first reinforcing layer embedded therein and having a first hardness, the main tubular member including a proximal end and a mating distal end;
a second tubular member formed of a material free of a reinforcing layer and having a second hardness which is less than the first hardness of the main member, the second tubular member including a mating proximal end, which is secured to the mating distal end of the main member and a mating distal end;
a third tubular member formed of an elastomeric material having a second reinforcing layer embedded therein and having a third hardness which is lower than the second hardness of the second tubular member, the third tubular member including a mating proximal end, which is secured to the mating distal end of the second tubular member, and a mating distal end;
a fourth tubular member formed of a material free of a reinforcing layer and having a fourth hardness which is lower than the third hardness of the material of the third tubular member, the fourth tubular member including a mating proximal end, which is secured to the mating distal end of the third tubular member, and a mating distal end; and a fifth terminal tubular member formed of a material free of a reinforcing layer and having a fifth hardness which is lower than the fourth hardness of the material of the fourth tubular member, the terminal member including a mating proximal end, which is secured to the mating distal end of the fourth tubular member, and a distal end.

37. An intravascular catheter comprising:

an elongate shall formed from at least two discrete tubular shaft members which have been joined together, the shaft including:

a first tubular member having a first flexibility along its length, the first tubular member being formed of a material having a first reinforcing layer embedded therein and having a first hardness, the first tubular member including a proximal end and a mating distal end, the first reinforcing layer terminating adjacent the mating distal end;

a second tubular member having a second flexibility along its length, the second tubular member formed of a material having a second reinforcing layer embedded therein and having a second hardness, the second tubular member including a mating proximal end and a mating distal end, the second reinforcing layer terminating adjacent the mating proximal end; and a bond member secured to the mating distal end of the first tubular member and the mating proximal end of the second tubular member, wherein the bond member has a third hardness intermediate to the first hardness of the first tubular member and the second hardness of the second tubular member.

38. The intravascular catheter of claim 37 wherein the third hardness of the bond member is medial the first hardness of the first tubular member and the second hardness of the second tubular member.

39. In an intravascular catheter having a first discrete tubular member with a first hardness and a first flexibility along its length joined to a second discrete tubular member having a second hardness and a second flexibility along its length, an improvement comprising:

a bond member positioned between the first tubular member and the second tubular member with a first lap joint bond securing the bond member to the first tubular member and a second lap joint bond securing the bond member to the second tubular member, wherein the bond member has a third hardness intermediate the first hardness of the first tubular member and the second hardness of the second tubular member and wherein the material of the first tubular member and the material of the second tubular member is mixed across the bond member to form a homogeneous bond.

* * * * *

UNITED STATES PATENT AND TRADEMARK OFFICE
CERTIFICATE OF CORRECTION

PATENT NO. : 5,531,721

DATED : JULY 2, 1996

INVENTOR(S) : HENRY J. PEPIN, BRIAN J. SCOVIL, JEFFREY M. WELCH

It is certified that error appears in the above-indentified patent and that said Letters Patent is hereby corrected as shown below:

Col. 7, line 33, delete "shalt", insert --shaft--

Col. 8, line 22, delete "shall", insert --shaft--

Col. 9, line 4, delete "shall", insert --shaft--

Col. 13, line 9, delete "shall", insert --shaft--

Signed and Sealed this

Twenty-sixth Day of November 1996

Attest:

BRUCE LEHMAN

Attesting Officer     Commissioner of Patents and Trademarks